United States Patent [19]

Kaye

[11] 4,062,355

[45] Dec. 13, 1977

[54] DEVICE FOR USE IN EVALUATING THE LOWER LEG AND FOOT

[76] Inventor: Joshua Morley Kaye, 7309 N. Ashland Ave., Chicago, Ill. 60626

[21] Appl. No.: 675,641

[22] Filed: Apr. 9, 1976

[51] Int. Cl.² ............................................. A61B 5/09
[52] U.S. Cl. ................................... 128/2 S; 33/174 D
[58] Field of Search ............ 128/2 S, 2 R; 33/174 R, 33/174 D, 174 C

[56] References Cited

U.S. PATENT DOCUMENTS

| | | | |
|---|---|---|---|
| 2,535,787 | 12/1950 | Darby | 33/174 D |
| 2,645,025 | 7/1953 | Weinerman | 33/174 D |

*Primary Examiner*—Stephen C. Pellegrino
*Attorney, Agent, or Firm*—Haight, Hofeldt, Davis & Jambor

[57] ABSTRACT

A device for use in making biomechanical or orthopedic evaluations of the lower leg and foot employs a heel stationing arrangement to automatically provide a reference line parallel to the vertical bisection of the calcaneus bone. A forefoot measuring device is utilized to measure the angular deformity of the forefoot (varus or valgus) by determining the angular deviation of the plane of the ball of the foot with respect to a plane perpendicular to the heel reference line. The forefoot measuring arrangement is adaptable to measure either the plane of the ball of the foot as determined by all five rays or as determined by any desired grouping of rays, such as the second through the fifth rays. A rearfoot measuring arrangement measures the angular deformity of the rearfoot (varus or valgus) by determining the vertical bisection of the lower leg with respect to the heel reference line. Further, the device has an attachment to measure the dorsiflexion and plantarflexion of the foot about the ankle.

20 Claims, 4 Drawing Figures

U.S. Patent  Dec. 13, 1977  Sheet 1 of 2  4,062,355
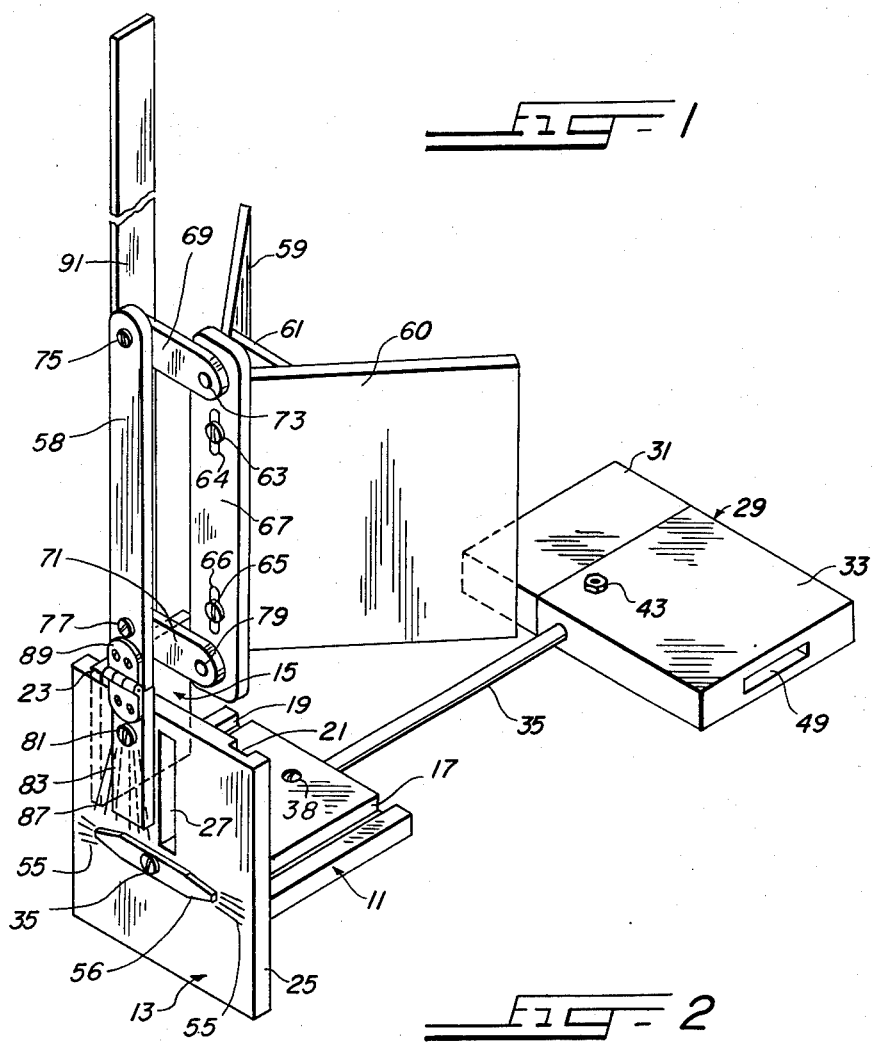

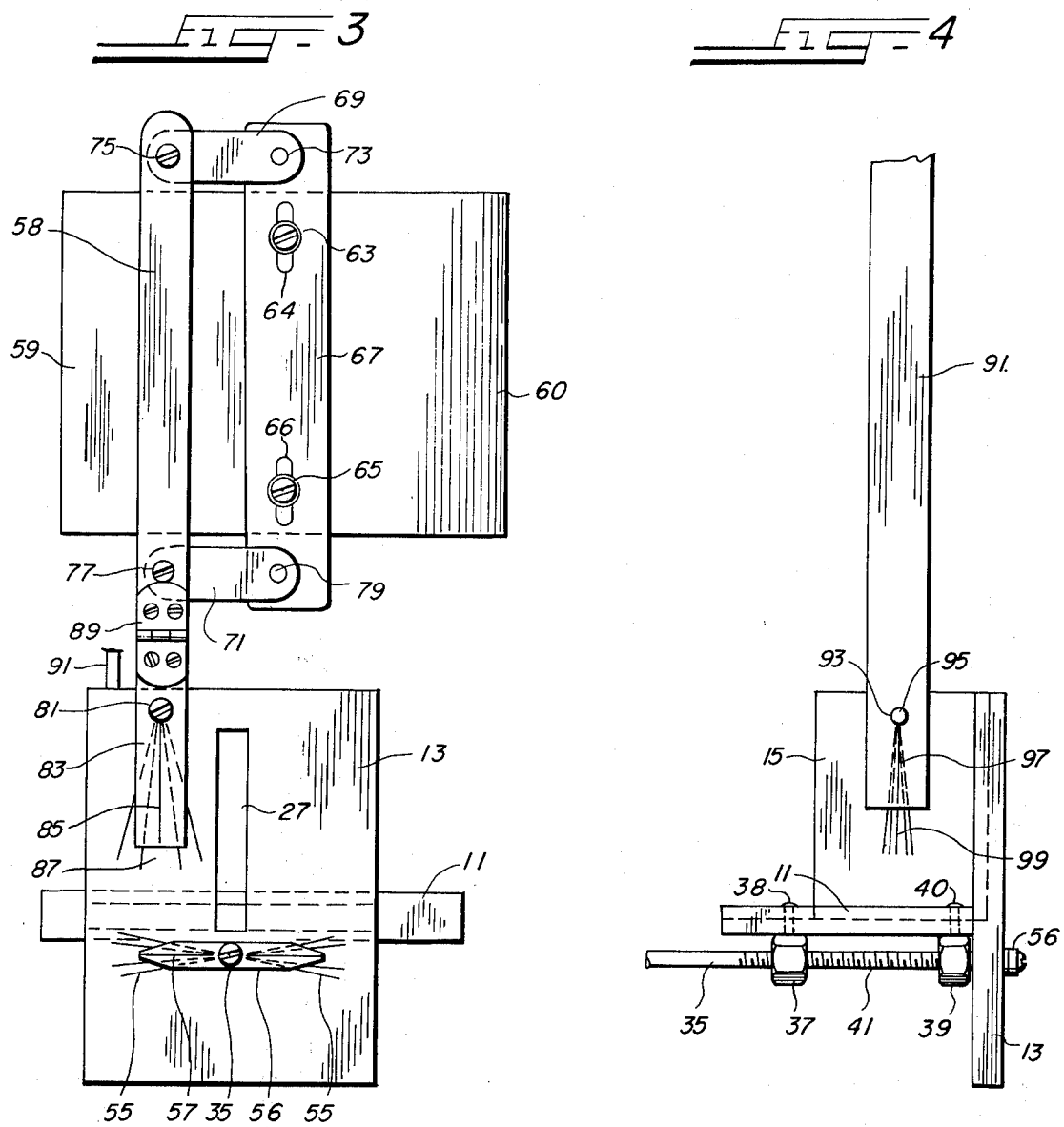

DEVICE FOR USE IN EVALUATING THE LOWER LEG AND FOOT

BACKGROUND OF THE INVENTION

1. Field of the Invention

This invention relates generally to a device useful in the analysis and treatment of structural or positional abnormalities in the foot and lower leg, and more specifically, this invention relates to a device for quickly and easily providing measurements of the varus and valgus of the rearfoot and forefoot, as well as the dorsiflexion and plantarflexion of the foot about the ankle axis.

2. Description of the Prior Art

Problems of the foot and lower leg can frequently be corrected, or at least compensated for or controlled, by the utilization of an appropriate device (such as a shoe insert or orthotic device). In more extreme cases, surgical correction may be required. In either circumstance, an appropriate biomechanical evaluation of the foot and lower leg is required.

The foot, ankle and lower leg are, like many other areas of the body, extremely complex in terms of the various interrelationships that affect the comfort, mobility and function of a person. However, there are certain interrelationships that have a significant overall effect and which can be determined in a quantitative sense. Three of these that are particularly pertinent to the foot and lower leg are forefoot deformity (varus or valgus), rearfoot deformity (varus or valgus) and the dorsiflexion and plantarflexion of the foot about the ankle. Varus and valgus are technical terms that signify, inter alia, a twisting or torsion of the forefoot or rearfoot in a desired plane. Varus (or inversion of the foot) is a position wherein the lateral side (outside) of the foot is on the ground, while the medial side (inside) is raised above the ground. Similarly, valgus (or eversion of the foot) is a position wherein the medial side of the foot is on the ground while the lateral side is raised above the ground. These positions can occur independently in the forefoot and in the rearfoot. Dorsiflexion is the position wherein the foot is flexed upwardly toward the shin or lower leg. Conversely, plantarflexion is the position wherein the foot is extended downward away from the shin or lower leg.

Measurement of these critical characteristics in the past has been very imprecise and subjective, while being often impossible to duplicate. Basically, the prior art procedure is to "eyeball" or visually determine a vertical bisection of the heel or calcaneus bone by palpation or feel of this bone. This vertical bisection would then be drawn on the skin of the patient and used as a reference for attempting to visually estimate the angular deviation of the forefoot and rearfoot.

While to the present day measurement of the rearfoot deformity is based upon a visual comparison of an "eyeballed" vertical bisection of the calcaneus and an "eyeballed" vertical bisection of the lower leg, there at least has been a minor advance in the measurement of forefoot deformity. Thus, at least one prior art device utilizes a pivoted plate under the ball of the foot to give an indication of the plane of the ball of the foot, but even this device still relies upon a comparison of a mechanically derived perpendicular to the plane of the ball of the foot with an "eyeballed" vertical bisection of the calcaneus or heel.

Obviously, the prior art leaves much to be desired in terms of providing reliable and accurate information upon which a biomechanical or orthopedic evaluation of the foot and lower leg can be based.

SUMMARY OF THE INVENTION

With the device of the present invention, the inaccuracies and vagaries of prior art measurements are obviated. This important advance is achieved by automatically and mechanically fixing a heel reference line that is parallel to the vertical bisection of the back or posterior surface of the calcaneus bone. This important result is achieved by utilizing a heel stationing structure that includes a base plate to receive the inferior or bottom surface of the heel, a rear plate against which the posterior or back surface of the heel is to be placed, and a side plate against which the medial or inside surface of the heel is to be placed. (The preferred utilization of the present invention involves the medial side of the foot and is so described herein, although it should be noted that the lateral side or outside of the foot could be used, if so desired.) In this fashion, the intersection of the rear plate and the side plate establishes a vertical reference line parallel to the vertical bisection of the calcaneus bone. Thus, the vertical bisection of the calcaneus is automatically and mechanically established for comparison purposes, without the requirement of any guesswork and with virtually complete reproducibility.

Having established this heel reference line, the device provides for mechanically and accurately measuring the forefoot and rearfoot deformities. A forefoot measuring arrangement utilizes a forefoot measuring plate that is affixed to an axle which is rotatably mounted in the base plate. To provide an indicating arrangement, the end of the axle at the base plate extends through the rear plate and has an appropriate marker fastened thereon. An appropriate scale, calibrated in arcuate degrees, is located on the rear surface of the rear plate adjacent to the marker, so that the angular deformity of the forefoot can be quickly and easily determined. When the heel is properly stationed in contact with the base plate, the rear plate and the side plate, the plane of the ball of the foot is established by the forefoot measuring plate, and the angular orientation of the plane of the ball of the foot with respect to a plane perpendicular to the heel reference line, and hence the angular deformity (varus or valgus) of the forefoot, may be read directly from the indicating scale on the rear plate. An important aspect of the forefoot measuring plate is that it may be constructed in portions which are relatively displaceable, such as by a sliding connection on a bar positioned in appropriate slots in the portions. By separating the portions, the plane of the forefoot may be selectively determined by desired groupings of rays. For example, in the preferred embodiment hereof the plane of the first ray, which involves the great toe and its associated metatarsal and tarsal bones, is removed from the plane of the other four rays. In this fashion, it is possible to obtain separate measurements of forefoot varus or valgus as determined by all five rays or as determined by any desired group of rays, such as the second through the fifth rays. The forefoot measuring plate is rotatable 180° to permit its use on either the right or left foot. Also, the associated indicating arrangement is bi-lateral or reversible to permit utilization of the same scale for measurements of either foot.

Rearfoot angular deviation is measured by mechanically establishing a rearfoot measuring line parallel to the vertical bisection of the lower leg. To achieve this result, a lower leg bisectional representing structure, such as a pair of planar surfaces located at an acute angle with respect to one another, is utilized to establish the rearfoot measuring line. With the planar surfaces, the actual vertical bisection of the lower leg may be determined, although any line parallel to this would serve equally well. A vertical support is pivotally connected on the rear plate, while an appropriate mounting arrangement is utilized for lower leg bisectional representing structure so that it may be moved relative to the vertical support, while still maintaining a parallel relationship between the rearfoot measuring line and the axis of the vertical support in order to accomodate various leg sizes and positions. In this preferred embodiment, a parallelogram arrangement is utilized. A hinge in the vertical support permits accomodation of various leg sizes and positions with respect to the plane of the rear plate. The other end of the vertical support includes a marker, which is associated with an appropriate scale calibrated in arcuate degrees. Therefore, by placing the planar surfaces against the lower leg in the appropriate manner, the rearfoot angular deformation (varus or valgus) may be directly read off the scale on the rear plate.

In addition to the forefoot and rearfoot varus and valgus measurements, the present invention also provides for a mechanically accurate measurement of dorsiflexion and plantarflexion. The side plate is removably located in one of a pair of grooves formed in the base plate. These grooves are each located adjacent an edge of the base plate and extend perpendicularly from the rear plate, in which there are aligned grooves to provide an additional securing structure for the side plate. With this arrangement, the side plate need only be moved from one groove to the other to permit measurement of either the right or left foot.

For purposes of the dorsiflexion measurement, the side plate is moved, preferably but not necessarily, from the medial side (inside) to the lateral side (outside) of the heel. A pivot pin is formed on the side wall to mate with an appropriate pivot opening in a dorsiflexion measuring arm. The dorsiflexion measuring arm is located appropriately along the lower leg, while an indicating arrangement is provided at the end of the dorsiflexion measuring arm on the other side of the pivot pin by an appropriate marker adjacent an appropriate scale calibrated in arcuate degrees formed on the side plate. When the foot is dorsiflexed (or flexed upward), the forefoot measuring plate is maintained on the ball of the foot so that the amount of dorsiflexion can be read off the scale. The same procedure can be employed when the foot is plantar-flexed (or flexed downward), if desired.

Accordingly, applicant's device quickly, automatically and accurately provides measurement of the forefoot varus and valgus, rearfoot varus and valgus and dorsiflexion and plantar-flexion. This device clearly eliminates the guesswork and inaccuracies of prior art measurements, as well as greatly reducing the time required for such measurements.

These and other objects, advantages and features of this invention will hereinafter appear, and for purposes of illustration, but not of limitation, an exemplary embodiment of the subject invention is shown in the appended drawing.

BRIEF DESCRIPTION OF THE DRAWING

FIG. 1 is a perspective view of a device constructed in accordance with the present invention.

FIG. 2 is a top plan view of the device of FIG. 1.

FIG. 3 is a back elevational view of the device of FIG. 1.

FIG. 4 is a partial side elevational view of the device of FIG. 1.

DETAILED DESCRIPTION OF THE PREFERRED EMBODIMENT

With reference now to FIG. 1, the features of the present invention may be observed. The heel stationing structure includes a base plate 11, a rear plate 13 and a side plate 15. These plates may be formed of any appropriate material, preferrably of a hard plastic material which is relatively lightweight and yet durable. Base plate 11 is adapted to receive the inferior or bottom surface of the heel.

A pair of grooves 17 and 19 are formed in the base plate adjacent opposite sides thereof. These grooves 17 and 19 are adapted to selectively receive the side plate 15, so that the device may be used for measuring either the right foot or the left foot. As illustrated in FIG. 1, the side plate 15 is in groove 19 and hence adapted for right foot measurements, as side plate 15 is placed along the medial or inside surface of the heel for forefoot and rearfoot varus and valgus measurements in this preferred embodiment, although it is possible to locate side plate 15 on the lateral side, if so desired. To provide additional positioning security, grooves 17 and 19, and the bottom side of side plate 15, may be formed in the shape of an inverted "V," so that side plate 15 would be slid in and out.

Rear plate 13 is secured to the back of base plate 11 and has a pair of grooves 21 and 23 aligned with grooves 17 and 19, respectively, in base plate 11. Grooves 21 and 23 serve to receive the ends of end plate 15 to secure it in position in grooves 17 and 19. As shown in this preferred embodiment, rear plate 13 has a portion 25 extending below the plane of the base plate, which would normally be desirable, although not necessary. A slot 27 is formed in rear plate 13. This slot 27 is not directly relevant to the measurements discussed herein, as it provides for the observation of a vertical bisection of the calcaneus drawn on the skin of the heel, or for the drawing of such a vertical bisection, for other purposes than the measurements discussed herein.

When the heel is stationed in contact with the base plate 11, the rear plate 13 and the side plate 15, a heel reference line is defined by the intersection of the rear plate 13 and side plate 15. This heel reference line is parallel to the vertical bisection of the calcaneus bone or heel bone. Accordingly, a reference for both the forefoot and rearfoot varus and valgus measurements is automatically and accurately established.

Forefoot deformations may be measured with the utilization of a forefoot measuring plate 29, which has a first ray portion 31 and a second through fifth ray portion 33. (Other divisions to permit measurements based upon other groupings of rays could also be utilized, but this arrangement is that which would normally provide the greatest utility.) Forefoot measuring plate 29 is mounted on an axle 35. As may best be seen in FIG. 4, axle 35 is rotatably mounted on base plate 11. While this rotatable mounting is illustrated as a pair of nuts 37 and 39, secured by mounting bolts or pins 38 and 40, respectively, in which a threaded portion 41 of axle 35 revolves, any appropriate rotatable mounting (bearing or bushing) would suffice. Forefoot measuring plate 29 is securely affixed to axle 35 in any fashion that would prevent rotation of axle 35 in plate 29, although in the preferred embodiment hereof this connection is schematically illustrated by the bolt and nut arrangement 43.

As may best be seen in FIG. 2, portions 31 and 33 of plate 29 are relatively displaceable. Although any appropriate sliding connection could be utilized, such as a pair of metal rods, in this preferred embodiment a bar 45 is located in appropriate slots 47 and 49 located in portions 31 and 33, respectively. The portion of bar 45 in slot 47 is securely affixed to the portion 31, while the bar 45 is free to slide in slot 49. As illustrated by the dotted lines in FIG. 2, pulling bar 45 from slot 49 causes the inner edge 51 of portion 31 to be displaced from the inner edge 53 of portion 33. This displacement is sufficiently large to receive the first ray of the foot, so that the angular position of plate 29 is determined by the plane of the four other rays, absent the first ray. In this fashion, the varus and valgus of the forefoot can be measured for the plane of the ball of the foot as determined by all five rays and as determined by the second through the fifth rays.

The angular deviation of the forefoot from a predetermined norm (i.e., the varus or valgus) may be read directly from a scale 55 located on the rear plate 13. The scale 55 is calibrated in arcuate degrees, so that the angular deviation (and hence the varus or valgus) may be directly read from the scale. This angular deviation is established by a marker 57 (FIG. 3) formed in a transparent pointer 56 located on the end of axle 35. Again, any appropriate type of indicating arrangement could be utilized, although the particular form shown herein has proved especially useful in this preferred embodiment. It may be noted that the identical scale portions 55 on either side of pointer 56 permit 180° rotation of the forefoot measuring plate 29. This is quite important, as plate 29 is rotated 180° to permit measurements on both the right and left feet. This complete rotation is necessary to permit the measurements for the plane of the ball of the foot as established by the second through the fifth rays only for both right and left feet (or any other desired grouping of rays).

With respect to the measurement of rearfoot deformity, it is necessary to obtain a line parallel to the vertical bisection of the lower leg for comparison to the heel reference line to determine the angular deviation of the rearfoot from the desired norm. While this could be accomplished by visually determining the vertical bisection of the leg, since the fixed reference line for the heel will greatly improve the accuracy even with this approach, it is preferable to have some means for mechanically determining a rearfoot measuring line parallel to the vertical bisection of the lower leg and automatically determining the relationship between this line and the heel reference line, which will yield the varus or valgus of the rearfoot. One approach that has been sucessfully employed by applicant, and is broadly disclosed herein, involves the utilization of a parallelogram secured on a vertical support that is pivotally mounted on the rear plate. Since opposing sides of the parallelogram will always be parallel, use of the vertical support as one of the sides means that the opposing sides can be utilized to establish the vertical bisection of the lower leg. Due to the parallel relationship, the angular deviation of the vertical support from a true vertical will directly indicate the angular deviation (varus or valgus) of the rearfoot with respect to the heel reference line.

While the foregoing approach is a considerable advance over the prior art, applicant has gone one step further in the preferred embodiment and has further reduced the possibility of error by automatically determining the vertical bisection of the lower leg. Thus, on a pivotally mounted vertical support 58, a lower leg bisectional representing arrangement employing two planar surfaces 59 and 60 is disclosed. Planar surfaces 59 and 60 are secured together to form an angle. This angle may be any angle less than 180°, although an angle in the vicinity of 90° would usually be preferred. This structure is then mounted on the vertical support 58 so that the bisectional plane of the angle will be parallel to the axle 35.

Planar surfaces 59 and 60 may be secured together in any appropriate fashion. In this preferred embodiment, the ends of planar surfaces 59 and 60 are mitered and fastened with an appropriate adhesive. A strengthening and supporting plate 61 is utilized both for fixing and holding the angle between the planar surfaces 59 and 60 and to provide an arrangement for mounting the lower leg bisectional representing structure. This mounting may take any appropriate form, but is disclosed herein as nut and bolt arrangements 63 and 65, which may be vertically slidable in slots 64 and 66, respectively, formed in a mounting arm 67. Mounting arm 67 is mounted in any appropriate way so that it maintains a fixed angular relationship with respect to the vertical support 58 as the lower leg bisectional representing arrangement is moved. In this preferred embodiment, such a fixed relationship is maintained by making the support arm 67 the opposing side of a parallelogram with the vertical support 58. Vertical support 58 and mounting arm 67 are connected together by linking arms 69 and 71, which are pivotally connected to support 58 and arm 67 at each end thereof by any appropriate means, illustrated generally herein at 73, 75, 77 and 79. With this arrangement, the planar surfaces 59 and 60, when placed against the lower leg, will automatically determine the vertical bisection of the lower leg and establish a rearfoot measuring line parallel thereto. By means of the parallelogram arrangement, this rearfoot measuring line will be reflected in the angular position of the vertical support 58. Thus, the device provides for the accomodation of various leg sizes and positions as they affect the location of the vertical bisection of the lower leg along the plane of the rear plate.

The pivotal mounting for vertical support 58 is illustrated at 81. The portion of vertical support 58 that extends in the opposite direction from pivot 81 than the portion of support 58 upon which the lower leg bisectional representing structure is mounted includes a marker 85. While this marker 85 can be any appropriate type of indicator, such as a pointer, in this preferred embodiment, marker 85 is a vertical line formed on a transparent portion of support 58. A corresponding scale 87, calibrated in arcuate degrees, is formed on rear plate 13. Thus, the marker 85 and scale 87 provide an indicating arrangement for demonstrating the angular deviation between the rearfoot measuring line established by plates 59 and 60 and the heel reference line established by base plate 11, rear plate 13 and side plate 15.

It may be noted that a hinge 89 is located in the vertical support 55. The purpose of this hinge 89 is to permit the accomodation of various leg sizes and positions, as they affect the location of the vertical bisection of the lower leg in a plane perpendicular to the plane of the rear plate. In addition, hinge 89 permits folding the vertical support down to make a smaller structure for packing and carrying, as well as getting the lower leg bisectional representing structure out of the way when making forefoot or dorsiflexion measurements.

In addition to the forefoot and rearfoot varus and valgus measurements, the present invention also has an attachment that may be utilized to measure the dorsiflexion and plantarflexion of the foot. This is achieved by a dorsiflexion measuring arm 91, which is pivotally mounted on side plate 15. Incidentally, it should be noted that the placement of the dorsiflexion measuring arm in these drawings is actually for measurement of the left foot, while the forefoot and rearfoot measurements are made of the right foot. The reason for this is that (in this preferred embodiment) side plate 15 is placed on the lateral or outside of the foot for the dorsiflexion measurement, while for the rearfoot and frontfoot measurements it is placed on the medial or inside of the foot. Also, with the rectangular side plate 15 utilized in this preferred embodiment, it would normally be placed in the position shown in the drawings only for the dorsiflexion measurement, while for the forefoot and rearfoot measurements it would normally be rotated 90° to extend farther along the medial side of the foot. Since the side plate 15 has to be transferred from the medial to the lateral side of the foot when making the dorsiflexion measurement anyway (in this preferred embodiment), the rotation of the side plate 15 in this preferred emobodiment does not create any difficulty. Of course, if so desired, the shape of side plate 15 could be altered, such as by making it into a square form, so that it could be used in the same position for all measurements.

Dorsiflexion measuring arm 91 has a pivotal opening 93 therein, which is adapted to receive a pivot pin 95 located on side plate 15. An indicating arrangement for the dorsiflexion and plantarflexion measurements is provided by a marker 97 and a scale 99. Marker 97 is a vertical line formed on a transparent end of the dorsiflexion measuring arm 91 that extends below the pivot pin 95. The marker 97 indicates on the scale 99, which is calibrated in arcuate degrees, the angle of dorsiflexion or plantarflexion. (While this device can give both dorsiflexion and plantarflexion measurements, it will be primarily utilized in measuring dorsiflexion, and hence this term is frequently used in the generalized sense herein of including plantarflexion.)

To measure dorsiflexion, the dorsiflexion measuring arm 91 is appropriately located along the leg while the foot is flexed upwardly about the ankle. The forefoot measuring plate 29 is maintained in contact with the ball of the foot, so that the angular degrees of dorsiflexion may be read directly from scale 99.

As with the base plate 11, rear plate 13 and side plate 15, any suitable material may be utilized for the other parts of this device. However, in this preferred embodiment, all parts, with the exception of the metal axle 35 and any metallic connectors or hinge portions, are formed of a suitable plastic material. This plastic material should, of course, be sufficiently strong to prevent any distortion or warping, but yet light enough to make the overall weight of the device not become burdensome.

It should be understood that various modifications, changes and variations may be made in the arrangements, operations and details of construction of the elements disclosed herein without departing from the spirit and scope of this invention.

I claim:

1. A device for use in rendering evaluations of the lower leg and foot of a person comprising:
    heel stationing means to automatically provide a heel reference line parallel to the vertical bisection of the posterior surface of the calcaneus bone when the heel is placed therein;
    forefoot measuring means pivotally mounted on said heel stationing means to automatically determine and provide an indication of the angular deviation of the plane of the ball of the foot from a plane perpendicular to said heel reference line, thus producing forefoot varus and valgus measurements; and
    rearfoot measuring means pivotally mounted on said heel stationing means to determine a rearfoot measuring line parallel to the vertical bisection of the lower leg and automatically provide an indication of the angular deviation between said heel reference line and said rearfoot measuring line, thus producing rearfoot varus and valgus measurements.

2. A device as claimed in claim 1 and further comprising dorsiflexion measuring means romovably mounted on said heel stationing means.

3. A device as claimed in claim 1 wherein said heel stationing means comprises:
    a base plate to receive the inferior surface of the heel;
    a rear plate connected to said base plate and located in a plane perpendicular thereto, said rear plate adapted to have the posterior surface of the heel positioned thereagainst;
    a side plate to have a side of the heel positioned thereagainst; and
    a pair of grooves formed in the top surface of said base plate and adapted to selectively receive said side plate, each of said grooves located adjacent an associated side of said base plate and extending transversely to said rear plate, placement of said side plate in the groove adjacent the desired side of the foot and positioning of the heel in contact with said base plate, said rear plate and said side plate producing a heel reference line parallel to the vertical bisection of the posterior surface of the calcaneus bone.

4. A device as claimed in claim 3 and further comprising:
    a pivot pin located on said side plate;
    a dorsiflexion measuring arm having a pivot opening located thereon, said pivot opening adapted to receive said pivot pin; and
    indicating means to provide an angular dorsiflexion measurement upon the foot being flexed upwardly about the ankle, said dorsiflexion measuring arm being maintained parallel to the lower leg with said side plate on a desired side of the foot, while the heel is contacting said base plate.

5. A device as claimed in claim 3 wherein said forefoot measuring means comprises:
    an axle extending parallel to the plane of said base plate and rotatably mounted on said base plate;
    a forefoot measuring plate mounted on said axle at a position under the ball of the foot; and
    indicating means located on said axle to demonstrate the angular deviation of the plane of the ball of the foot from the plane of said base plate, when the heel is contacting said base plate, said rear plate and said side plate.

6. A device as claimed in claim 3 wherein said rearfoot measuring means comprises:

a vertical support pivotally mounted on said back plate and extending upwardly therefrom;

lower leg bisectional representing means to provide said rearfoot measuring line;

mounting means to mount said lower leg bisectional representing means on said vertical support to permit relative movement therebetween without varying the angular relationship between said rearfoot measuring line and the vertical axis of said vertical support; and indicating means to demonstrate the angular deviation between said rearfoot measuring line and said heel reference line.

7. A device for use in rendering biomechanical and orthopedic evaluations of the lower leg and foot of a person comprising:

a base plate to receive the inferior surface of the heel;

a rear plate connected to said base plate and located in a plane perpendicular thereto, said rear plate adapted to have the posterior surface of the heel located thereagainst;

a side plate to have the medial side of the heel positioned thereagainst;

a pair of grooves formed in the top surface of said base plate and adapted to selectively receive said side plate, each of said grooves located adjacent an associated side of said base plate and extending transversely to said rear plate, placement of said side plate in the groove adjacent the medial side of the foot and positioning of the heel in contact with said base plate, said rear plate and said side plate producing a heel reference line parallel to the vertical bisection of the calcaneus bone;

an axle extending parallel to the plane of said base plate and rotatably mounted on said base plate;

a forefoot measuring plate mounted on said axle at a position under the ball of the foot;

first indicating means located on an end of said axle which extends beyond said rear plate, said first indicating means demonstrating the angular deviation of the plane of the ball of the foot from a plane perpendicular to said heel reference line, when the heel is contacting said base plate, said rear plate and said side plate, thus producing forefoot varus and valgus measurements;

an elongated vertical support pivotally mounted on said rear plate and extending upwardly therefrom;

lower leg bisectional representing means to provide a rearfoot measuring line parallel to the vertical bisection of the lower leg;

a parallelogram arrangement to mount said lower leg bisectional representing means on said vertical support for movement of said lower leg bisectional representing means with respect to said vertical support without disrupting the parallel relationship between said rearfoot measuring line and the axis of said vertical support;

a hinge located in said vertical support to permit motion of said lower leg bisectional representing means backward from said rear plate;

second indicating means to demonstrate the angular deviation of said rearfoot measuring line from said heel reference line, when the heel is contacting said base plate, said rear plate and said side plate, thus producing rearfoot varus and valgus measurements;

a pivot pin located on said side plate;

a dorsiflexion measuring arm having a pivot opening located adjacent one end thereof, said pivot opening adapted to receive said pivot pin; and third indicating means to provide an angular dorsiflexion measurement upon the foot being flexed upwardly about the ankle, said dorsiflexion measuring arm being maintained parallel to the lower leg with said side plate on the lateral side of the foot, while the ball of the foot is positioned on said forefoot measuring plate and the heel is contacting said base plate.

8. A device as claimed in claim 7 wherein:

said first indicating means comrises a first scale, calibrated in arcuate degrees and located on said rear plate, and a first marker located on an end of said axle that extends through said rear plate;

said second indicating means comprises a second scale, calibrated in arcuate degrees and located on said rear plate, and a second marker located on an end of said vertical support that extends from the pivotal mounting thereof in a direction away from said lower leg bisectional representing means; and said third indicating means comprises a third scale, calibrated in arcuate degrees and located on said side plate, and a third marker located on an end of said dorsiflexion measuring arm that extends from said pivot pin in a direction away from the lower leg.

9. A device as claimed in claim 7 wherein said forefoot measuring plate comprises:

a first ray portion; and a second through fifth ray portion, said portions being relatively displaceable to permit separate measurements of the varus and valgus of the forefoot as determined by the first through fifth rays and as determined by the second through fifth rays.

10. A device as claimed in claim 9 wherein said portions are interconnected by a connecting bar located in aligned slots in said portions, so that displacement of said portions away from each other permits removal of the first ray from the plane of said forefoot measuring plate.

11. A device as claimed in claim 7 wherein said lower leg bisectional representing means comprises:

a first planar member; and a second planar member, said first and second planar members being connected at an acute angle with respect to one another, the bisectional plane of said acute angle being parallel to said axle so that placement of both said planar members against the lower leg automatically produces a vertical bisection of the lower leg.

12. A device as claimed in claim 7 and further comprises:

a slot formed in said rear plate to permit the marking of a vertical bisectional line on the heel and the observance of such a line already marked thereon; and grooves formed in said rear plate adjacent said grooves in said base plate to help secure said side plate in place.

13. A device for use in rendering evaluations of the lower leg and foot of a person comprising:

heel stationing means to automatically provide a heel reference line parallel to the vertical bisection of the posterior surface of the calcaneus bone when the heel is placed therein;

an axle pivotally mounted on said heel stationing means;

a forefoot meansuring plate mounted on said axle and located under the ball of the foot; and indicating means to show the angular deviation of the plane of the ball of the foot from a plane perpendicular to said heel reference line, thus producing forefoot varus and valgus measurements.

14. A device as claimed in claim 13 wherein said heel stationing means comprises:

a base plate to receive the inferior surface of the heel;

a rear plate connected to said base plate and located in a plane perpendicular thereto, said rear plate adapted to have the posterior surface of the heel positioned thereagainst;

a side plate to have a side of the heel positioned thereagainst; and a pair of grooves formed in the top surface of said base plate and adapted to selectively receive said side plate, each of said grooves located adjacent an associated side of said base plate and extending transversely to said rear plate, placement of said side plate in the groove adjacent a desired side of the foot and positioning of the rearfoot in contact with said base plate, said rear plate and said side plate producing a heel reference line parallel to the vertical bisection of the calcaneus bone.

15. A device as claimed in claim 14 wherein:

said axle extends parallel to the plane of said base plate and is rotatably mounted on said base plate;

said forefoot measuring plate is mounted on said axle at a position under the ball of the foot; and said indicating means is located on the end of said axle adjacent said heel stationing means to demonstrate on said heel stationing means the angular deviation of the plane of the ball of the foot from the plane of said base plate, when the heel is contacting said base plate, said rear plate and said side plate.

16. A device as claimed in claim 15 wherein said forefoot measuring plate comprises:

a first ray portion upon which at least one ray would normally be located; and a second ray portion upon which at least one other ray would normally be located, said first and second portions being relatively displaceable to permit separate measurements of the varus and valgus of the forefoot as determined when said first portion supports its associated ray or rays and when said first portion does not support its associated ray or rays.

17. A device for use in rendering evaluations of the lower leg and foot of a person comprising:

heel stationing means to automatically provide a heel reference line parallel to the vertical bisection of the posterior surface of the calcaneus bone when the heel is placed therein;

a vertical support pivotally mounted on said heel stationing means;

lower leg bisectional representing means mounted on said vertical support to provide a rearfoot measuring line parallel to the vertical bisection of the lower leg; and indicating means to show the angular deviation between said rearfoot measuring line and said heel reference line, thus producing rearfoot varus and valgus meansurements.

18. A device as claimed in claim 17 wherein said heel stationing means comprises:

a base plate to receive the inferior surface of the heel;

a rear plate connected to said base plate and located in a plane perpendicular thereto, said rear plate adapted to have the posterior surface of the heel positioned thereagainst;

a side plate to have a side of the heel positioned thereagainst;

A pair of grooves formed in the top surface of said base plate and adapted to selectively receive said side plate, each of said grooves located adjacent an associated side of said base plate and extending transversely to said rear plate, placement of said side plate in the groove adjacent a desired side of the foot and positioning of the rearfoot in contact with said base plate, said rear plate and said side plate producing a heel reference line parallel to the vertical bisection of the calcaneus bone.

19. A device as claimed in claim 18 wherein:

said vertical support is pivotally mounted on said back plate and extends upwardly therefrom; and mounting means mount said lower leg bisectional representing means on said vertical support to permit relative movement therebetween without varying the angular relationship between said rearfoot measuring line and the vertical axis of said vertical support.

20. A device as claimed in claim 19 and further comprising a hinge located in said vertical support to permit motion of said lower leg bisectional representing means backward from said rear plate to permit accomodation of various leg sizes and positions.

* * * * *